(12) United States Patent
Yost et al.

(10) Patent No.: US 10,390,704 B2
(45) Date of Patent: Aug. 27, 2019

(54) SYSTEMS AND METHODS FOR MEASURING PHASE DYNAMICS AND OTHER PROPERTIES

(71) Applicant: U.S.A as represented by the Administrator of the National Aeronautics and Space Administration, Washington, DC (US)

(72) Inventors: William T. Yost, Newport News, VA (US); John H. Cantrell, Williamsburg, VA (US); Daniel F. Perey, Yorktown, VA (US)

(73) Assignee: United States of America as represented by the Administrator of NASA, Washington, DC (US)

( * ) Notice: Subject to any disclaimer, the term of this patent is extended or adjusted under 35 U.S.C. 154(b) by 661 days.

(21) Appl. No.: 15/065,089

(22) Filed: Mar. 9, 2016

(65) Prior Publication Data
US 2016/0262621 A1    Sep. 15, 2016

Related U.S. Application Data

(60) Provisional application No. 62/131,397, filed on Mar. 11, 2015.

(51) Int. Cl.
*A61B 5/00* (2006.01)
*A61B 5/03* (2006.01)

(52) U.S. Cl.
CPC .......... *A61B 5/0051* (2013.01); *A61B 5/031* (2013.01); *A61B 5/7246* (2013.01); *A61B 5/7278* (2013.01)

(58) Field of Classification Search
CPC ...... A61B 5/031; A61B 5/0051; A61B 5/7278
See application file for complete search history.

(56) References Cited

U.S. PATENT DOCUMENTS

| 4,458,214 A | 7/1984 | Lakomy |
| 5,214,955 A * | 6/1993 | Yost ..................... G01N 29/075 |
| | | 374/119 |

(Continued)

OTHER PUBLICATIONS

Ueno, Toshiaki, et al., "Noninvasive Assessment of Intracranial Pressure Waveforms by using Pulsed Phase Lock Loop Technology," Journal of Neurosurgery 103, Aug. 2005, pp. 361-367, vol. 103.

(Continued)

*Primary Examiner* — Adam J Eiseman
*Assistant Examiner* — Raymond P Dulman
(74) *Attorney, Agent, or Firm* — Andrea Z. Warmbier; Robin W. Edwards; Mark P. Dvorscak

(57) ABSTRACT

Systems and methods for measuring phase dynamics and other properties (e.g. intracranial pressure) are disclosed. For example, the system may generate a reference waveform and a measurement waveform using digital synthesizers, each waveform having an identical constant frequency but also a relative phase shift. Next, system may send a tone-burst, via a transducer, into a sample (e.g. a skull or a bonded material), and then receive a reflected tone-burst in response. Then, a phase difference between the received tone-burst and the measurement waveform may be determined with a linear phase detector. Next, the phase shift of the measurement waveform may be adjusted, by the determined phase difference, such that there is no longer any phase difference between the received tone-burst and the adjusted measurement waveform generated by the appropriate digital synthesizer. A similar adjustment may occur after subsequent tone-bursts, allowing accurate monitoring of continuously variable phase relationships.

8 Claims, 7 Drawing Sheets

(56) References Cited

U.S. PATENT DOCUMENTS

| | | | | |
|---|---|---|---|---|
| 5,617,873 | A * | 4/1997 | Yost | A61B 5/031 33/511 |
| 6,413,227 | B1 * | 7/2002 | Yost | A61B 5/031 600/561 |
| 6,475,147 | B1 | 11/2002 | Yost et al. | |
| 6,746,410 | B2 | 6/2004 | Yost et al. | |
| 7,381,186 | B2 | 5/2008 | Ueno et al. | |
| 2006/0025686 | A1 | 2/2006 | Ueno et al. | |
| 2006/0079773 | A1 * | 4/2006 | Mourad | A61B 5/031 600/438 |
| 2007/0038095 | A1 * | 2/2007 | Greenleaf | A61B 8/00 600/438 |
| 2007/0093702 | A1 * | 4/2007 | Yu | A61B 5/14551 600/326 |

OTHER PUBLICATIONS

McSkimin, H. J., "Pulse Superposition Method for Measuring Ultrasonic Wave Velocities in Solids," The Journal of the Acoustical Society of America, Jan. 1961, pp. 12-16, vol. 33, No. 1.

Yost, William T., et al.,"Fundamental aspects of pulsed phase-locked loop technology-based methods for measurement of ultrasonic velocity," The Journal of the Acoustical Society of America, 91, 1992, pp. 1456-1468.

Yost, William T., et al., "Constant Frequency Pulsed Phase-Locked Loop Instrument for Measurement of Ultrasonic Velocity," Rev. Sci. Instr. 62, 1991, pp. 2451-2456.

* cited by examiner

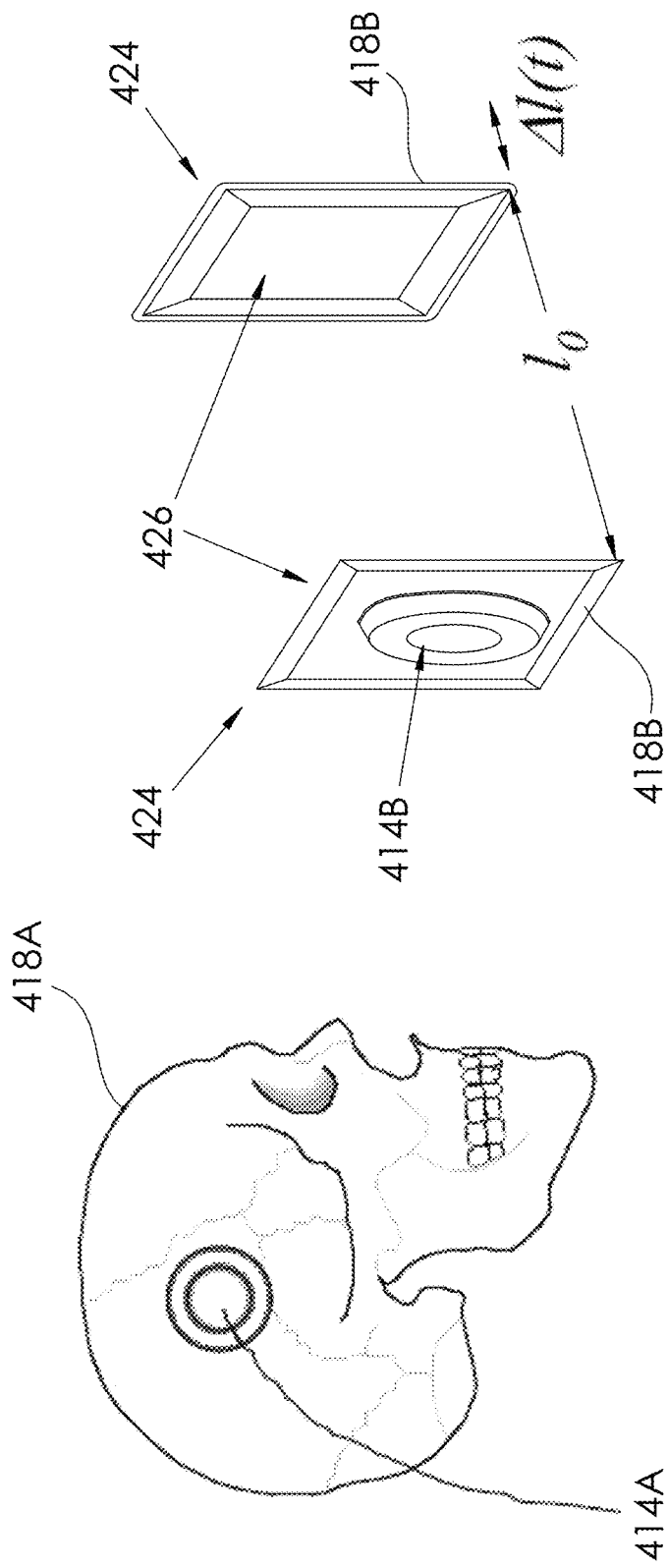

SYSTEMS AND METHODS FOR MEASURING PHASE DYNAMICS AND OTHER PROPERTIES

CROSS-REFERENCE TO RELATED PATENT APPLICATION(S)

This patent application claims the benefit of and priority to U.S. Provisional Patent Application No. 62/131,397, filed on Mar. 11, 2015, the contents of which are hereby incorporated by reference in their entirety.

STATEMENT REGARDING FEDERALLY SPONSORED RESEARCH OR DEVELOPMENT

The invention described herein was made by employees of the United States Government and may be manufactured and used by or for the Government of the United States of America for governmental purposes without the payment of any royalties thereon or therefore.

TECHNICAL FIELD

Certain aspects of the disclosure relate to systems and methods for measuring phase differences, variable phase relationships, and/or other properties (e.g. intracranial dynamics and/or intracranial pressure).

BACKGROUND OF THE INVENTION

The non-invasive evaluation of intracranial pressure may provide important medical information when evaluating head injuries (e.g. concussions) or effects from other medical conditions (e.g. strokes, brain tumors, and meningitis). Prior methods of this analysis relied on pulsed phrase-locked loop technology ("PPLL"), and relied on a quadrature phase detector to detect phase changes between a reference oscillator path and a second path resulting from a wave passing though the cranial vault, and then reestablish quadrature between the two paths. Whenever the second path changed in any way, these instruments adjusted the reference oscillator frequency until quadrature was re-established. The PPLL instrument would then record this change in frequency and use it to estimate the phase change that occurred in the second path. These instrument's measurement of frequency, f, is related to the ultrasonic wave speed v and path length l by Equation 1:

$$\frac{\Delta f}{f} = \frac{\Delta v}{v} - \frac{\Delta l}{l}$$

These methods, however, suffer from drawbacks, including problems with accuracy, precision, noise level and stability. For example, other elements in the measurement paths, such as coaxial cables, amplifiers, signal splitters, ultrasonic transducers and so on, also affect a signal's phase as the frequency changes. This creates errors as well as uncertainties, as the PPLL systems operate under that assumption that the quadrature phase detectors respond only to phase changes in the signal path relative to the reference oscillator path. What's more, reflections from the skull also shift phase due to frequency changes, and therefore also create unintended and unaccounted phase-shift contributions to the systems output. Another drawback is that the quadrature phase detector prevents the measurement technology from measuring phase differences linearly, and therefore cannot provide numerical output in phase.

BRIEF SUMMARY OF THE INVENTION

This Summary provides an introduction to some general concepts relating to this disclosure in a simplified form, where the general concepts are further described below in the Detailed Description. This Summary is not intended to identify key features or essential features of the disclosure.

In accordance with one example aspect of the disclosure, measurement systems are disclosed. In some examples, the systems include at least one processor and an oscillator module. The oscillator module may be a digital oscillator module and may include one or more direct digital synthesizers. In some embodiments, the module may include a first and at least a second direct digital synthesizer. In embodiments, the system may also include a linear phase detector, a tone-burst module, a transducer (e.g. an ultrasonic transducer, such as a piezoelectric transducer) communicatively coupled to the tone-burst module and configured to be attached to a sample, and memory. In some examples of the system, the processor, the digital oscillator module, the linear phase detector, and the tone-burst module are all communicatively coupled to each other.

In some examples of a system, including the one discussed immediately above, may comprise a transducer configured to be removably attached to a sample. In certain embodiments, the system may comprise a non-transitory computer readable medium (which may also be referred to herein as a storage memory or a memory), having computer-readable instructions that, when executed by the at least one processor, may cause a first direct digital synthesizer to generate a reference waveform having a constant frequency when the transducer is attached to a sample. Using a second direct digital synthesizer, a measurement waveform having the same constant frequency as the reference waveform may be generated, The measurement waveform may be shifted and therefore have an initial phase shift relative to the reference waveform. The system may determine, using the tone-burst module, and based on the reference waveform, a tone-burst wave sequence (for example, a number of cycles of the reference waveform). Subsequently, the system may send, for example, via the transducer), a tone-burst into the sample that is based on the determined tone-burst wave sequence, and then the system receives, using the transducer, a received tone-burst from the sample.

In various embodiments, a system, including a system described above, may determine, using the linear phase detector, a phase difference between the received tone-burst and the measurement waveform (i.e. determines what additional shift there is in the received tone-burst relative to the initial shift already present in the measurement waveform relative to the reference waveform). Then, the system may adjust, using the second digital synthesizer, the initial phase shift of the measurement waveform, by the determined phase difference, to an adjusted phase shift relative to the reference waveform, such that there is no longer any phase difference between the received tone-burst and the measurement waveform, and such that the adjusted measurement waveform may be used in subsequent analysis (and may be subsequently further adjusted, if desired).

In certain examples, the instructions, when executed by at least one processor, cause the system to convert the determined phase difference to a first digital value, and then record, using the processor, the first digital value in the memory. The conversion may be performed by the linear phase detector. In some examples, the computer-executable instructions, when executed by a processor, further cause the system to send, using the transducer, and based on the tone-burst wave sequence, a plurality of additional tone-bursts into the sample. In these examples, the system may consequently receive, using the transducer, a plurality of received tone-bursts (e.g. receive a tone-burst from the sample after each sent tone-burst, and then sending another tone-burst into the sample).

In some example embodiments, the system may further determine, using the linear phase detector, a plurality of phase differences between the plurality of received tone-bursts and the measurement waveform. The phase shift of the measurement waveform may be further adjusted, using the second digital synthesizer, after each tone-burst is received and prior to the subsequent tone-burst being sent into the sample, wherein the adjustment is based on the determined phase difference between the measurement waveform and the most recently received tone-burst, such that there is no longer any phase difference between the most recently received tone-burst and the adjusted measurement waveform. Thus, the measurement waveform may be continually adjusted before each additional tone-burst is sent into the sample, such that the determined phase difference from the next received tone-burst is determined by comparison to the measurement waveform, as it was adjusted based on the previously received tone-burst.

In certain example embodiments, computer-executable instructions, when executed by a processor, may cause a system to convert, using the linear phase detector, the plurality of determined phase differences (and/or a plurality of total phase differences between the adjusted measurement waveforms and the reference waveform) to a plurality of digital values and then record, using the processor, the plurality of digital values in the memory. In some examples, the constant frequency is between 100 KHz and 15 MHz, however, is not limited to this range.

In certain embodiments, the sample may be or otherwise include a human head, and the computer-executable instructions, when executed, cause a processor to determine, based on at least the determined phase difference and/or differences, one or more of: rate of skull volume expansion, total fluid volume present in the skull, and/or intracranial pressure. These are merely examples and other characteristics are within the scope of this disclosure.

In various embodiments, the sample comprises an article including two dissimilar, bonded materials, and the computer-executable instructions, when executed, further cause one or more systems to determine, based on at least the determined phase difference and/or differences, one or more bond characteristics of the article or a portion thereof. In some examples, the system may record a digital value every ten milliseconds or less. In certain embodiments, recordation may be variable and/or adjustable.

In accordance with another example aspect of the disclosure, measurement methods are disclosed. In some examples, the methods include generating, with a first direct digital synthesizer, a reference waveform having a constant frequency, and generating, using a second direct digital synthesizer, a measurement waveform having the same constant frequency as the reference waveform and an initial phase shift relative to the reference waveform. In some examples, the methods then include determining, based on the reference waveform, a tone-burst wave sequence, and subsequently sending, using a transducer, and based on the determined tone-burst wave sequence, a tone-burst into a sample and consequently receiving, using the transducer, a received tone-burst from the sample.

Next, example embodiments include determining a phase difference between the received tone-burst and the measurement waveform and adjusting, using the second digital synthesizer, the initial phase shift of the measurement waveform, by the determined phase difference, to an adjusted phase shift relative to the reference waveform, such that there is no longer any phase difference between the received tone-burst and the measurement waveform.

In certain examples, the methods also include sending, using the transducer, a plurality of additional tone-bursts into the sample, and consequently receiving, using the transducer, a plurality of received tone-bursts. Then, the methods may include determining a plurality of phase differences between the plurality of received tone-bursts and the measurement waveform, wherein the phase shift of the measurement waveform is further adjusted, using the second digital synthesizer, after each tone-burst is received and prior to the subsequent tone-burst being sent into the sample. The adjustment may be based on the determined phase difference between the measurement waveform and the most recently received tone-burst, such that there is no longer any phase difference between the most recently received tone-burst and the adjusted measurement waveform.

In certain method examples, the constant frequency is between 100 KHz and 15 MHz. In some embodiments, the sample is a human head, and the methods include determining, based on at least the plurality of determined phase differences, one or more of rate of skull volume expansion, total fluid volume present in the skull, and intracranial pressure. In other examples, the sample is an article including two dissimilar, bonded materials, and the method includes determining, based on at least the plurality of determined phase differences, one or more bond characteristics. In some examples, a delay between the plurality of additional tone-bursts is 20 milliseconds or less, while in other it is 8 milliseconds or less.

In certain method examples, the methods include generating, with a first direct digital synthesizer, a reference waveform having a constant frequency, and generating, using a second direct digital synthesizer, a measurement waveform having the same constant frequency as the reference waveform and an initial phase shift relative to the reference waveform. In these examples, the methods may then include sending, using a transducer, a plurality of tone-bursts into a sample and receiving, using the transducer, a plurality of received tone-bursts from the sample. Next, in these embodiments, the methods may include determining a plurality of phase differences between the received tone-bursts and the measurement waveform. In these examples, the phase shift of the measurement waveform is continually updated, using the second digital synthesizer, after each tone-burst is received and prior to the subsequent tone-burst being sent into the sample, such that there is no longer any phase difference between the most recently received tone-burst and the updated measurement waveform.

In certain examples, there is a delay between each tone-burst, and each of the plurality of determined phase differences substantially matches a phase change that occurs in the sample during each delay. In some examples, each of the plurality of determined phase differences matches a phase change that occurs in the sample during each delay.

In certain of these examples, the sample is a human head, and the method further including determining, based on at least the plurality of determined phase differences, one or more of rate of skull volume expansion, total fluid volume present in the skull, and intracranial pressure. In some of these embodiments, a delay between the plurality of additional tone-bursts is 50 milliseconds or less, and the constant frequency is between 500 KHz and 10 MHz.

These summary descriptions are merely provide examples of the systems (and components thereof), methods and/or method steps that may be performed in one or more embodiments. In certain embodiments, systems and methods include additional combinations or substitutions. To that end, other details and features will be described in the sections that follow. Any of the features discussed in the embodiments of one aspect may be features of embodiments of any other aspect discussed herein. Moreover, additional and alternative suitable variations, features, aspects and steps will be recognized by those skilled in the art given the benefit of this disclosure.

BRIEF DESCRIPTION OF THE SEVERAL VIEWS OF THE DRAWINGS

Example embodiments of the disclosure will now be described by way of example only and with reference to the accompanying drawings, in which:

FIGS. 4A and 4B illustrate example components of an embodiment of a measurement system and the resulting wave propagation path.

DETAILED DESCRIPTION OF THE INVENTION

Figure 1:
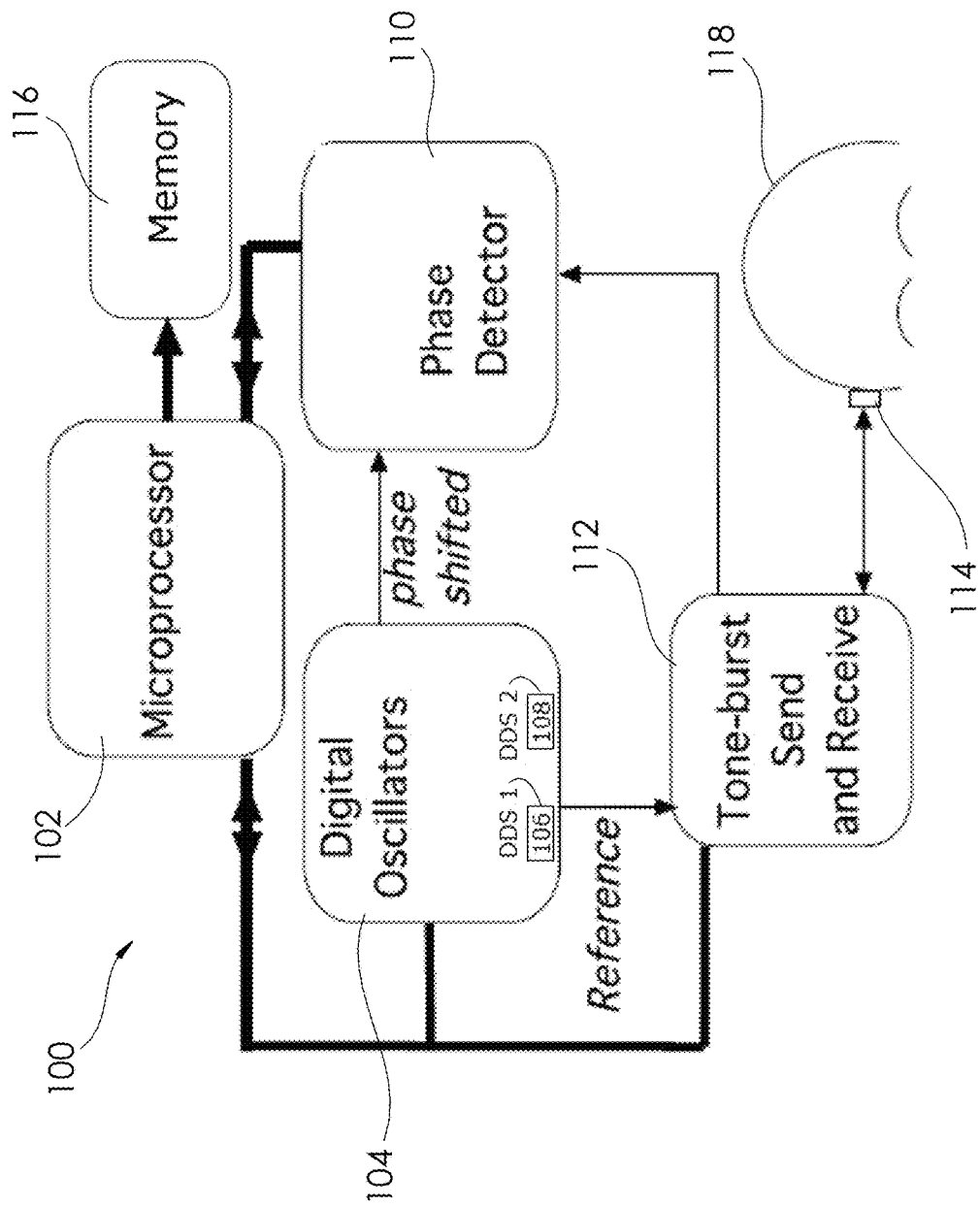
FIG. 1 illustrates a schematic diagram of an example embodiment of a measurement system.

The examples, systems, apparatuses and methods of described herein provide systems and/or methods for measuring properties, relationships, and/or dynamics. These and other aspects, features and advantages of the disclosure or of certain embodiments of the disclosure will be further understood by those skilled in the art from the following description of example embodiments. In the following description of various examples, reference is made to the accompanying drawings, which form a part hereof. It is to be understood that other modifications may be made from the specifically described methods and systems without departing from the scope of the present disclosure.

In accordance with one aspect, measurement systems are provided. As described in more detail below, these systems may offer new analytical capabilities for assessment of, e.g., intracranial dynamics and/or other properties. One or more disclosed systems may be utilized to monitor of trans-cranial expansion and related physiological phenomena in humans resulting from variations in intracranial pressure caused by injuries to the head and/or brain pathologies. In some examples, the systems utilize a constant frequency pulse phase-locked loop ("CFPPLL") to, e.g., measure skull expansion caused by pressure and its variations in time. When compared with prior systems, the disclosed systems provide a more accurate and robust measurement capability with improved bandwidth. In accordance with various embodiments, these systems provide new analytical approaches for assessing the physiology of skull expansion under pulsatile cerebral blood flow, as described in more detail herein. Further, although reference is given to a human skull, those skilled in the art will appreciate that other skulls, including mammalian and/or non-mammalian are envisioned within the scope of this disclosure. Further, physiological and anatomical characteristics and properties of other body regions may be determined using one or more systems and methods disclosed herein without departing from the scope of this disclosure.

As some examples, the dynamic quantities assessable with these systems include, but are not limited to: skull volume expansion and total fluid volume current in the skull. These systems may also allow the analytical generation of the intracranial pressure waveform. Disclosed systems may utilize a circuit capable of detecting any continuously variable phase relationship, measuring and digitizing this value to high accuracy, and adjusting the phase comparison circuitry by, for example, commands based on the highly accurate digital values, and may store these values in a computer-readable memory or digital memory. In certain examples, this arrangement may result in higher accuracy and higher precision of the phase adjustment, and may result in a lower noise level of instrument operation. In certain examples, operational circuit stability is also improved, resulting in more stable operations for data collection.

FIG. 1 shows a schematic diagram of an example embodiment of a system that may be utilized in accordance with one or more embodiments. In the illustrated embodiment of FIG. 1, the system 100 is utilizing operating parameters and components for measuring trans-cranial expansion of a skull. In this example, the system 100 includes a processor (one or more additional processors may be incorporated as well) 102 and a digital oscillator module 104. The oscillator module may include a plurality of direct digital synthesizers. For example, oscillator module 104 includes a first direct digital synthesizer 106 and a second direct digital synthesizer 108. The example system also includes a linear phase detector 110, a tone-burst module 112, a transducer 114 communicatively coupled to the tone-burst module and configured to be attached to a sample, and memory 116 that is communicatively coupled to at least the processor 102. In this and other examples, the transducer may be an ultrasonic transducer. In some examples, modules/components may be combined into a single module/component. In certain examples, components of a module may be connected as separate and/or discrete components, e.g. two direct digital synthesizers may be individually connected to the system circuitry, rather than as a module including two synthesizers). In this example of the system, the processor, the digital oscillator module, the linear phase detector, and the tone-burst module are all communicatively coupled to each other. The transducer may be configured to be attached to a sample, such as a human head or an article (where the sample may be present in an analysis chamber, such as a thermodynamic environmental control chamber). In this example, the transducer 114 is shown as being operatively connected to a sample 118 that is a human head. In this and other examples, the processor may issue commands and receive data along a bus, such as a bidirectional bus, illustrated with heavy black lines (e.g. all the microprocessor connections utilize a bus, or all processor connections with the exception of the memory connection utilize a bus).

The memory 116 may include one or more computer-readable storage media. The memory may store computer-readable instructions (as in memory 116 of the example embodiment of FIG. 1) and/or computer-readable data (i.e., information that may or may not be executable), whether in one medium or in a combination of mediums. In some examples, the media may include one or more hard disks, CD-ROMs, optical storage devices, magnetic storage devices, and/or any combination thereof. The transducer 114 may be capable of generating an ultrasonic tone-burst, and in some examples, comprises a piezoelectric transducer. As described in more detail below, the digital oscillator module 104 may include two direct digital synthesizers ("DDS") running at the same frequency, and only differing in phase.

The systems disclosed herein may be configured to perform various methods and/or method steps, as illustrated in the example methods described herein. In some examples of the system, the memory stores computer-readable instructions that, when executed by at least one processor, such as processor 102, cause the processor to provide an output, which in turn results in the system to perform certain actions. Thus, the system components, in operation, may provide a synthesized system capable of shifting the phase upon command from the microprocessor (for example, in response to a detected/determined phase difference), which may control the operation of the entire system. When the system is attached to a sample (via a transducer), the actions allow the system to take measurement data related to the sample. For example, system 100 may generate, using a first direct digital synthesizer (e.g. "DDS 1" 106 of FIG. 1), a reference waveform having a constant frequency (e.g. a continuous sine wave).

The system may also generate, using a second direct digital synthesizer (e.g. "DDS 2" 108 of FIG. 1), a measurement waveform having the same constant frequency as the reference waveform, but where the measurement waveform is shifted and therefore has an initial phase shift relative to the reference waveform. The phase shift between the synthesizers may be initially set by command from the microprocessor (for example, the processor may implement a saved value, use a value specifically entered by a user using a graphical user interface, or may select one a plurality of saved values based on the desired application). In certain embodiments, the phase shift may be further adjusted during system use, as described herein, by a processor command. In some example embodiments, the phase shift value is determined from data sent to the microprocessor from the phase detector, e.g. a phase shift is adjusted or updated based on data from the linear phase detector.

In some examples, the reference frequency is set to the transducer resonant frequency. Many frequencies are contemplated, and the reference frequency may be selected based on the type of analysis to be performed by the systems. For example, the reference frequency may be approximately 500 KHz, in, e.g. systems for measuring intracranial properties and/or dynamics. As another example, the reference frequency may be approximately 10 MHz in, e.g. systems for analyzing bonds and/or other articles, such as articles with two dissimilar materials. In some examples, the reference frequency is 400-600 KHz, or 250-750 KHz, or 100 KHz-1 MHz. In certain examples, the reference frequency is 9-11 MHz, 7-13 MHz, 9.5-10.5 MHz, 1-5 MHz, or 5-10 MHz. In certain embodiments, the constant frequency is between 100 KHz and 15 MHz. In certain examples, the reference frequency is 750 KHz or below, 500 KHz or below, or 250 KHz or below. In other examples, it is 250 KHz or above, 500 KHz or above, or 1 MHz or above. In various embodiments, the frequency is 10 MHz or above, 12 MHz or above, or 15 MHz or above, while in others it is 10 MHz or below, or 8 MHz or below. Additionally, certain systems may utilize heterodyning techniques and therefore use even further extended frequencies. For example, some systems may utilize a frequency 5 times larger (or more) than any of the reference frequency examples provided above, or 10 times larger (or more), or 20 times larger (or more). For example, the reference frequency may be approximately 200 MHz, approximately 100 MHz, or approximately 50 MHz. In some examples, the reference frequency may be 1 MHz or above, 10 MHz or above, or 50 MHz or above. In various examples, the reference frequency may be approximately 10-20 MHz, approximately 10-50 MHz, approximately 50-100 MHz, approximately 100-200 MHz, approximately 10-100 MHz, or approximately 50-200 MHz. Similarly, the frequency range may be one tenth or one twentieth of any of the example reference frequencies described herein. For example, the reference frequency may be approximately 25 KHz, approximately 50 KHz, approximately 100 KHz, or approximately 250 KHz. In some examples, the reference frequency may be 250 KHz or below, 100 KHz or below, 500 KHz or below, or 25 KHz or below. In various examples, the reference approximately may be approximately 25-50 KHz, approximately 25-100 KHz, approximately 50-100 KHz, approximately 50-250 KHz, approximately 50-500 KHz, or approximately 250-500 KHz.

Figure 6:
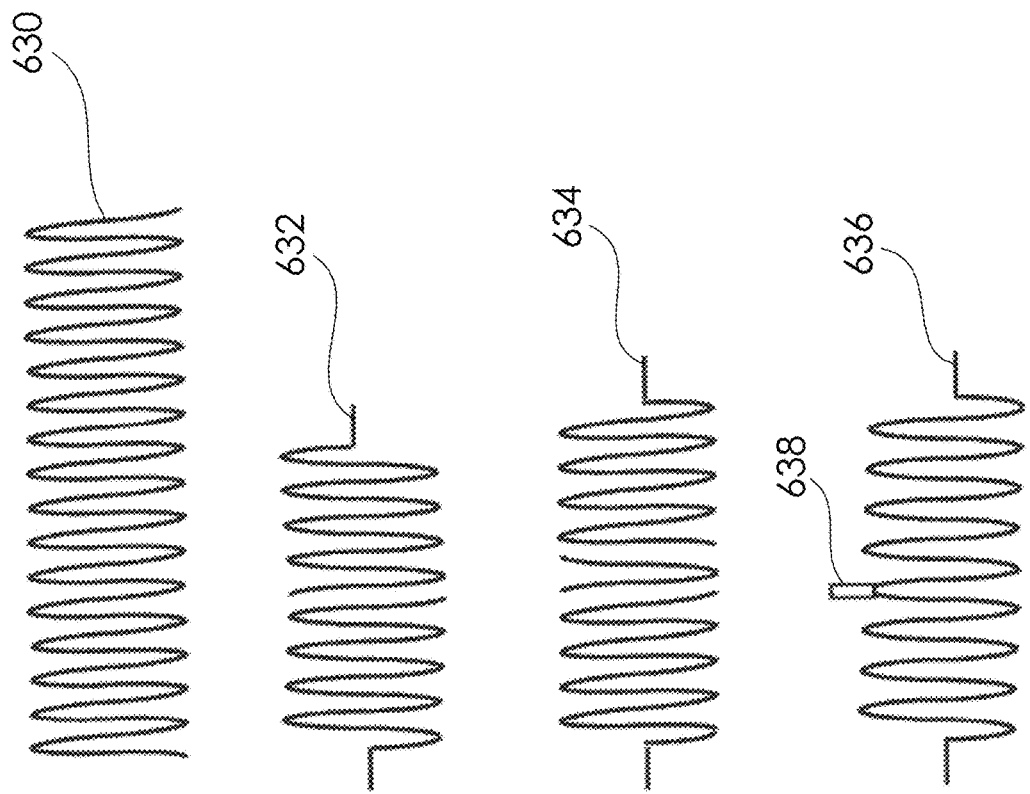
FIG. 6 illustrates example tone-burst and markers for use in example measurement methods and/or by example measurement systems.
Figure 7:
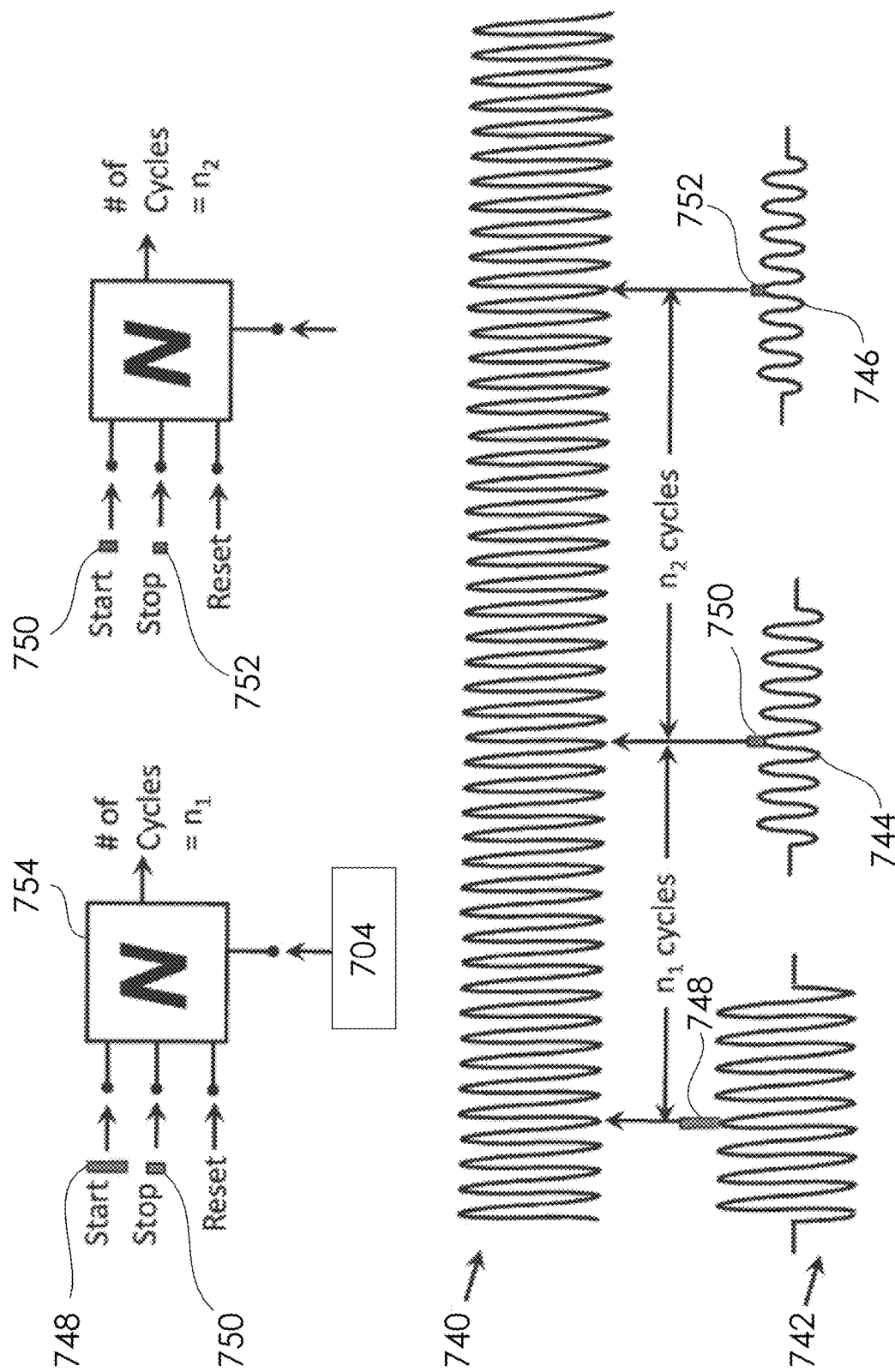
FIG. 7 illustrates example tone-bursts and echoes for use in example measurement methods and/or by example measurement systems.

Then, the system may determine, using the tone-burst module, and based on the reference waveform, a tone-burst wave sequence (for example, a sequence including number of cycles of the reference waveform). The tone-burst module may be a component or components configured to send and receive various tone-bursts. The radio frequency generated by the reference DDS (e.g. the DDS 1 in FIG. 1) may be sent to the tone-burst module (e.g. once the module is activated by the processor), which may then generate a tone-burst based on the received frequency (continuous wave signal) and other parameters (e.g. number of cycles, and so on). FIGS. 6 and 7 illustrate example tone-burst and markers used therein. For example, FIG. 6 illustrates an example DDS 1 reference signal output 630, used by the tone-burst module, and an example marker 638 (this marker being a pedestal) added by the tone-burst module to act as a reference for wave count for tone-burst example 636. A marker may be placed on or within a tone-burst to act as wave count reference. Tone-burst examples 632 (including a π phase shift) and 634 (including a 1 cycle π phase shift) are also illustrated as example markers within a tone-burst. In applications utilizing inertial terms, non-phase change markers may be used. The number of cycles may depend on the application and the specific measurement. The tone-burst may thus be formed form the first DDS input and including a number of cycles and a specific marker located, as appropriate for the application. In this manner, an electric tone burst may be determined by the module (or, e.g. by the module in combination with the processor) and then sent to a transducer, such as a piezoelectric transducer, where is it converted to an ultrasonic tone burst.

FIG. 7 illustrates an example of cycling counting based on the tone-burst based on pulse and echoes of a tone-burst in accordance with one embodiment. In this illustration, DDS 704 provides input to cycle counter 754, which utilizes a start marker 748, and stop marker 750, in which it may be configured to reset after the stop marker 740 is received. In one embodiment, a cycle counter may also reuse the marker 750 as a second start marker, and then another, marker, which for example may be a more diminished marker, e.g. see diminished marker 752, as a later stop marker. In this manner, a cycle counter may count multiple numbers of cycles. As illustrated, DDS output 740 may correspond to a tone burst 742 having the marker 748, and a n1 number of cycles may occur before the corresponding stop marker 750 of a received tone-burst echo 744 is received. As further illustrated, marker 750 may be reused as a start marker, such that n2 number of cycles may occur before the corresponding stop marker 752 of a received tone-burst echo 746 is received. As one non-limiting example, the number of cycles in the tone burst N, and the cycle chosen for measurement of phase n, may be equal to obtain wave count for a tone-burst round trip. The sample point may be moved to a cycle number until an echo's amplitude trace and phase trace is clear (e.g. which may be observed on an oscilloscope screen). The system, such as any disclosed herein, may determine the quantity of round-trip waves detected. The quantity may be divided by 2 to determine a quantity of waves across a cranium of the sample, and/or multiplied by 2 $\pi$ to obtain the phase of a path.

Figure 2:
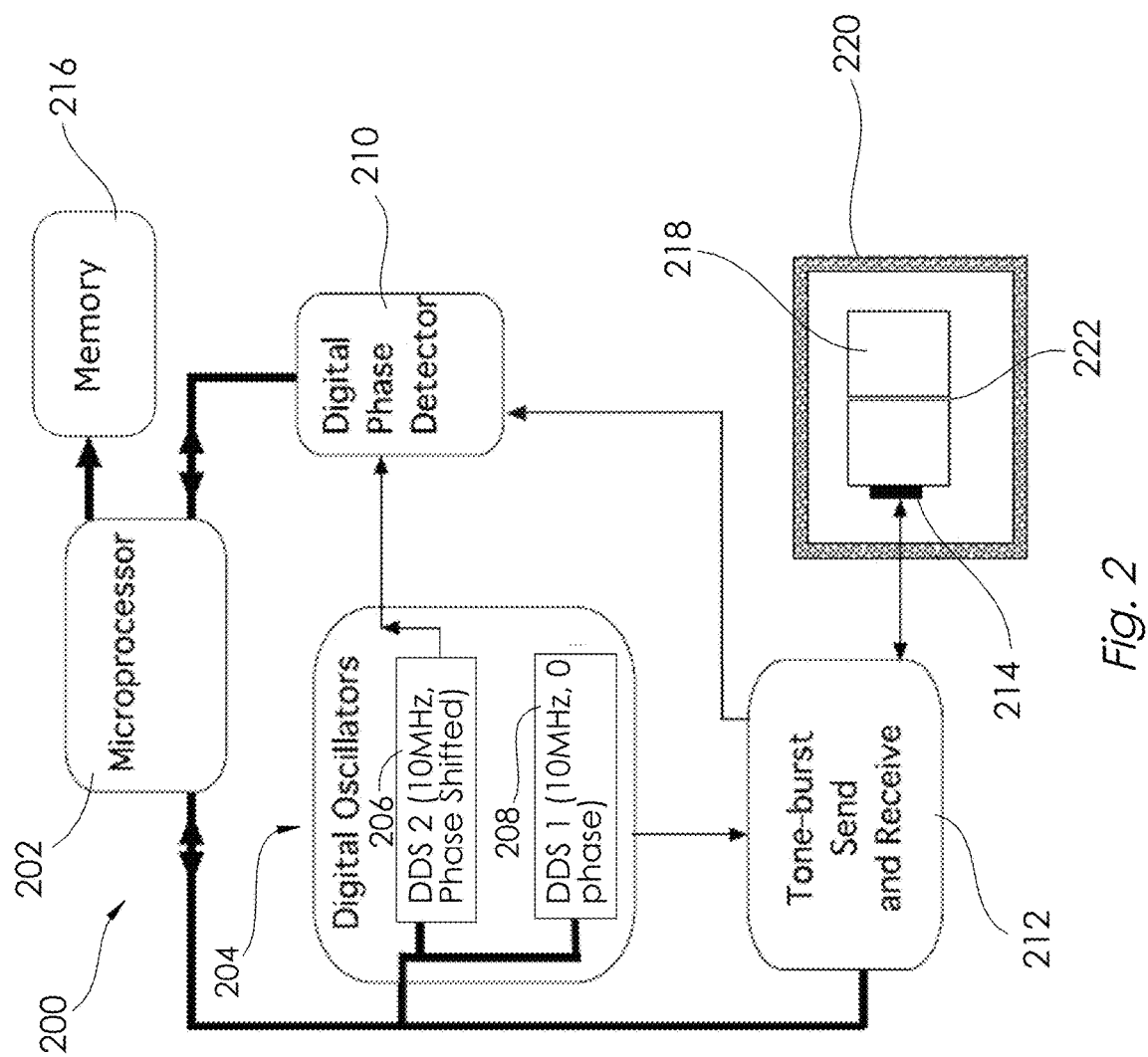
FIG. 2 illustrates a schematic diagram of another example embodiment of a measurement system.

Subsequently, the system may send, e.g., via the transducer, and based on the determined tone-burst wave sequence, a tone-burst into the sample. The transducer may generate an ultrasonic tone-burst that propagates to the region of interest, and that is then at least partially reflected back to the transducer (as examples, through and across the cranium and back to the transducer as shown in FIG. 1, or through an article/specimen to a bond region and back as shown in FIG. 2, as described in more detail below). The received ultrasonic tone-burst may be converted by the transducer to an electric tone burst, which is then sent, along with the measurement waveform output from the second digital oscillator, to the digital phase detector for phase comparison. That is, after conversion, the electrical conversion of the received reflections or "echoes" are phase-compared with the measurement waveform by the linear phase detector. Thus, after sending a tone-burst into the sample, the system may receive, using the transducer, a received tone-burst from the sample.

The system may then determine, using the linear phase detector, a phase difference between the received tone-burst and the measurement waveform (i.e. the system determines what additional shift there is in the received tone-burst relative to the initial shift already present in the measurement waveform relative to the reference waveform). The linear phase detector may convert phase differences between the reference waveform signal from the measurement waveform (e.g. the shifted signal from DDS 2 in FIG. 1) and the received tone-burst signal to a digital output. Operationally, the linear phase detector may measure the phase difference between the received tone-burst from the region of examination and the measurement waveform digital oscillator output. The phase comparison from the region of examination may be selected (e.g. may be set up manually or by an algorithm) and its value may be sent to a processor, such as processor 102. As a differential comparison, the difference in phase shift between, for example, two separate regions of a train or even groups of reflections may be measured. Indeed, as many physical phenomena, such as temperature coefficient of phase velocity, respond to the environmental variables, (e.g pressure and/or temperature) may show up as differential changes, many subjects and regions for examination may be analyzed with the system.

One of more computer-readable mediums may be located on one or more circuits within the system. In one embodiment, computer-readable instructions, (e.g. which may be part of the phase detection and measurement circuit, or installed into a dedicated memory), may be executed by a processor, such as processor 102, to determine the total phase shift. In certain embodiments, additional phase adjustment to the first quadrature point may be calculated by one or more processors, and the phase correction may be sent as a command to correct the total phase shift of the second DDS (relative to the first, reference, non-shifted DDS), where the total phase shift may also be stored in radians.

Thus, in some embodiments, the system then determine, using the linear phase detector, a phase difference between the received tone-burst and the measurement waveform (i.e. determines what additional shift there is in the received tone-burst relative to the initial shift already present in the measurement waveform relative to the reference waveform). Then, the system may adjust, using the second digital synthesizer, the initial phase shift of the measurement waveform, by the determined phase difference, to an adjusted phase shift relative to the reference waveform, such that there is no longer any phase difference between the received tone-burst and the measurement waveform, such that the adjusted measurement waveform may be used in subsequent analysis (and may be subsequently further adjusted, if desired). In some embodiments, the system may determine changes in the subject under measurement within very small phase differences, such as the associated physical changes in the test subject between quadrature point 1 (i.e. $\pi/2$) and the second quadrature point (i.e. $3\pi/2$). These embodiments may be useful, for example, in determining uniformity of nanotube alignment densities in newer materials. In some embodiments, the systems may use a third direct digital synthesizer to offset the phase reference by a known amount from the second direct digital synthesizer, and monitor, for example, physical phase changes within thin bonds to determine the physical properties of thin films. Thus, the system may monitor phase changes even when phases are very close together.

In example embodiments, the system then applies the negative of this shift as a correction to the phase-shifted oscillator providing the measurement waveform, so that the phase difference between the received ultrasonic wave and the oscillator becomes null. In operation, this condition may be maintained in time as the path length changes in time. The required phase shift change is negative when the path length change is positive, and vice versa. For example, the one or more computer-readable mediums may comprise computer-executable instructions to convert or otherwise modify the received value. In one implementation, it may be inverted to represent phase change in cranial expansion: as the skull expands, the phase change is negative to preserve quadrature, and this is the change in phase value for phase shift association with cranial expansion, and may be recorded with the corresponding time (and/or the total shift relative to the un-shifted reference waveform may be recorded). Thus, the system may be configured to adjust, using the second digital synthesizer, the initial phase shift of the measurement waveform, by the determined phase difference, to an adjusted phase shift relative to the reference waveform, such that there is no longer any phase difference between the received tone-burst and the measurement waveform, and such that the adjusted measurement waveform may be used in subsequent analysis, which may be repeated as needed or desired.

As mentioned above, in some examples, the system may be configured to send, e.g. via the transducer, and based on the tone-burst wave sequence, a plurality of additional tone-bursts into the sample. In these examples, the system may consequently receive, using the transducer, a plurality of received tone-bursts (e.g. receive a tone-burst from the sample after each sent tone-burst, and then sending another tone-burst into the sample). For example, the system may send, using the transducer, and based on the tone-burst wave sequence, a plurality of additional tone-bursts into the sample. In these examples, the system may consequently receive, using the transducer, a plurality of received tone-bursts (e.g. receive a tone-burst from the sample after each sent tone-burst, and then sending another tone-burst into the sample). In further embodiments, the system may further determine, using the linear phase detector, a plurality of phase differences between the plurality of received tone-bursts and the measurement waveform.

The phase shift of the measurement waveform may then be further adjusted, using the second digital synthesizer, after each tone-burst is received and prior to the subsequent tone-burst being sent into the sample, where the adjustment may be based on the determined phase difference between the measurement waveform and the most recently received tone-burst, such that there is no longer any phase difference between the most recently received tone-burst and the adjusted measurement waveform. Thus, the measurement waveform may be continually adjusted before each additional tone-burst is sent into the sample, such that the determined phase difference from the next received tone-burst is determined by comparison to the measurement waveform, as it was adjusted based on the previously received tone-burst. Then, using, e.g., the linear phase detector, the plurality of determined phase differences may then be recorded (and/or the plurality of total phase differences taking into account the initial phase shift), using the processor, as a plurality of digital values in the memory.

The change in the phase shift may be updated to keep the phase change exactly in step with the change in skull expansion over that time interval (or others). Taken together, the system therefore can deliver a stream of phase data that tracks skull expansion in time. In other example systems, (for example, as illustrated in FIG. 2) the recording of stress on a bond vs. time, the strain vs. time, and bond temperature vs. time, or a combination thereof, may be evaluated. If desired, it is contemplated that the time parameter may be eliminated such and system may determine time-independent information, such as bond modulus vs. temperature.

The processor may provide the timing and the commands that control the system set-up, and manage the implementation and use of the system; including data transfers among the connected components, and write data files associated with the system instrument outputs. These outputs may be derived from the raw data that is recorded and the data based operations needed to deliver a data stream. As one example, the above process may be recorded every 8 millisecond cycle (i.e. 125 recordings each second). This may accurately display, for example, skull expansion, which is driven by at least in part, the subject's heart rate, but other time periods may be used to account for an individual test subject, and the applicable heart rate. Given that skull expansion is nonlinear, in some examples, the sampling rate is approximately 40 per second, or greater, as significant harmonics may occur in the nonlinear expansion (e.g. 20th harmonic of 1 beat/second, which implies that 20 Hz may need to be resolved to some accuracy, and which, in turn, utilizing the Nyquist theorem, provides a sampling rate greater than 40/s). In some examples, the system records a digital value every ten milliseconds or less, or every five milliseconds or less. In others, it records a digital value every 15 milliseconds or less, every 20 milliseconds or less, every 25 milliseconds or less, every 50 milliseconds or less, or every 100 milliseconds or less. Thus, in some examples, the system may convert the determined phase difference to a digital value, and then record, using the processor, the digital value (or values from repeated analysis) in the memory. The conversion may be performed by the linear phase detector. Data inputs to the processor (or a control module containing one or more processors and, e.g. memory, a graphical user interface, input/output components, and the like) may include the transducer resonant frequency, the repetition rate, the number of wave cycles in a tone-burst, and the wave location at sampling of phase detection. These may be programmed into the system by a user depending on the particular application.

In some examples, the system may electronically store (e.g. in the memory) instruction sequence and information for system set-up and operation. This information may contain an operating frequency, a tone-burst width (number of cycles), a sample selection point (the number of cycles, starting with initiation of tone-burst to the counter where the digital phase detector value is recorded for data and setting of the second direct digital synthesize), and/or the time interval or delay between data points. The delay may be selected via consideration of waveform fidelity and ultrasonic dosage, and/or by other particular considers of the application. The pages may also contain instructions for internal controls, to be given along bus structure, and protocols for recording data in memory. The electronic information may also provide file formation structure and file/transfer protocols. In some examples, file transfer commands to USB or similar communication protocols or ports for organization, calculation, waveform operation, or plotting routines are used. For example, the system may plot phase signal as a function of time.

Outputs may include the initial phase, the total phase at lock point, the detected change in phase, the time of the lock point, and time (generally). The timing sequence implemented by, e.g. a processor (or other component of the system), and may include stating a pulse sequence determined from the repetition rate setting, forming a tone-burst with a number of cycles and a marker, and sending it to the transducer. A cycle counter may start with the marker insertion and/or when the tone-burst is sent to the transducer. The tone-burst pulse may then travel, echo, and be received, where the tone-burst marker may stop the cycle counter once received, and the system then performs the phase comparison. The cycle count number may be sent to the processor as well. The outputs may include phase change, the base phase, the total phase, and time. The cycle count may be multiplied by a to obtain radians in phase. The phase may be determined by dividing the radians by the ratio of pulse-travel distance to the physical path length (for example, if pulse-echo, the system divides by 2, as pulse-echo mode nit corresponds to the unperturbed or initial phase, while $2n\pi$ does in pitch-catch mode). This phase may be used for the phase detector output and correction for any off-resonance is made, and the result may then be sent to the processor and/or the memory.

Various embodiments may utilize different locations on the head/skull (e.g. measuring from top-to-base, side-to-side, and front-to-back (if needed, constant incremental phase shift compensation may be inserted into the DDS 2 to obtain maximum sensitivity for example by checking small pressure/front-to-back on the skull), or vice versa, or intermediate positions between these examples, or other locations, or with respect to other axis'). Placement of the transducer may be factored to account for the possibility of variations of skull stiffness with transducer location. Because these phase shift contributions cause errors and uncertainties with the frequency changes, as described above, the present disclosure relates systems that utilize a constant frequency pulsed phase-locked loop. The general relationships among the variables for these devices are given by Equation 2:

$$\frac{\Delta \phi}{\phi} = \frac{\Delta v}{v} - \frac{\Delta l}{l}$$

where ϕ is the wave's phase. With example CFPPLL systems, the phase shifting control mechanisms match only the phase changes that occur as when the skull path changes (i.e. the skull expands or contracts) relative to the reference oscillator, or substantially match such changes. For example, in some example systems and methods, there is a delay between each tone-burst sent to the sample, and each of the plurality of determined phase differences substantially matches a phase change that occurs in the sample during each delay. In some examples, each of the plurality of determined phase differences matches a phase change that occurs in the sample during each delay, while in others it may substantially match such changes. This may be important in such embodiments, to provide a high accurate representation of the phase change in time. Further, in these systems, the phase representation for control of the loop is continuously linear, as opposed to the quadrature representation of earlier models. In some examples, the systems may match phases at a point on the wave front being examined. In certain examples, quadrature points π/4 and 3π/4 may be utilized in the measurements.

There are numerous additional benefits of the systems disclosed herein. In example systems, the CFPPLL components, operating with a digitally-based circuitry coupled with the linear phase detector outlined, working as an ultrasonic interferometer a to provide a system that creates an electronic record of skull displacements in time, where an operator may choose the operating point of the phase comparison. Digital data operations may also be employed as the data is streaming from components of the system. The digitally based CFPPLL makes possible the measurement of skull expansion to a higher precision than previously possible. What's more, the ability to allow the user to select the reference phase shift difference, and the higher precision afforded by the digital measurement system allows a more robust, accurate analysis and a more comprehensive, broader range of applications that permits higher-order differentiation of phase changes in time.

These systems may provide desired topography with a flexible phase adjustment, where the adjustment may offer improved stability, and may further offer a linear output that ay removes secondary effects from the measurement outputs. And, as mentioned above, the systems may uniquely operate in constant frequency phase-measurements, thus avoiding some of the earlier approaches operated in frequency-shifting PPLL technologies.

In this manner, the phase measurement improvements of these systems may allow for higher definition (i.e. more precise) of the phase changes brought about by, for example, cranial expansion measurements. The systems may utilize highly linearized phase-detection circuits, as well as the highly stable direct digital synthesis oscillators. These changes allow for higher degrees of stable operation within ultrasonic applications, where abrupt changes often occur, and where other technologies become operationally unstable.

What's more, because of the relatively improved stability, the algorithms that relate these measurements to, e.g., physiologically significant measurements of skull volume expansion and the consequent change in total pulsatile blood flow to the brain, can be more reliably measured and determined for the first time. Earlier attempts used Doppler ultra-sonics to monitor blood flow velocity and use an approximation to estimate the blood flow through the brain by examination of blood speed through the anatomical feature, the blood vessel named the Circle of Willis, located in the central region of the brain.

The total effect of blood flow in time causes a dynamic skull expansion during the cardiac cycle, and this may be precisely measured via examples of measurement systems. What's more, the change in the phase shift may be updated to keep the phase change exactly in step with the change in cranial expansion, which is mathematically related to volume expansion. Taken together, examples of the system may deliver a stream of data that tracks volume expansion, blood flow (related to time derivative of cranial vault volume), and/or intracranial pressure in time. In certain examples, the data is sent to a digital file for further operations, for analysis, and/or for generation of related waveforms used in other analyses, for example other analyses useful to intracranial dynamics.

FIGS. 4A and 4B illustrate example samples being analyzed by system embodiments. In this example, FIG. 4B illustrates a transducer 414B (on left) being placed on a human head 418B so that the amplitude of the wave reflected from the opposite side of the skull is maximized. Here, surfaces 424 represent skin and/or hair and surfaces 426 represent bone dura of the skull. The transducer may be secured with any appropriate features or additional components, such as an elastic bandage wrapped around the skull. In this and other examples, the transducer 414B is placed on the side of the skull on a section slightly behind the ear. FIG. 4A similarly illustrates the mounting of a transducer 414A on sample 418A, in this case, on the side of a human head. FIG. 4B also illustrates the subsequent path of the ultrasonic wave launched into the skull. For example, a low power ultrasonic tone-burst may propagate through the outer tissue-bone-dura complex, travel across the cranial cavity, and reflect back to the transducer from the opposite side. The total path length l between the pulse transmitting and reflecting sides of the skull, schematically shown in FIG. 4B is given as (Equation 3):

$$l = l_0 + \Delta l(t)$$

where $l_0$ is the initial (unperturbed) distance and $\Delta l(t)$ is the cranial dimensional change in the direction of pulse propagation and in response to the pressure variations inside the skull. Since the ultrasonic phase speed does not change in the propagation medium, Equation 2 is written as (Equation 4):

$$\frac{\Delta \phi}{\phi} = -\frac{\Delta l}{l_0}$$

As the path length increases, the applied change in phase decreases to maintain the quadrature condition.

In some examples, the systems may measure intracranial dynamics with equation-based algorithms, and offer a path to measure or determine quasi-static intracranial pressure, along with the pulsatile-related intracranial pressure increments. Supportive measurements, such as time dependence of arterial pressure waveforms together with time dependent phase-change of trans-cranial expansions also serve as basis of noninvasive technique to measure intracranial pressure. By virtue of the relatively low number of components, the system may be easily and quickly set-up for measurement recording, thus bringing benefits to areas where trauma medical treatments are needed (e.g. trauma centers, emergency services, battlefields, and/or other locations where head injuries are treated), as well as in locations treating and/or managing brain pathologies, such as strokes, brain tumors, meningitis, and/or in the determination of severity of concussions. The non-invasive measurement of both static and/or dynamic intracranial pressures as provided by system examples may provide important information, especially for early diagnoses though, e.g., rapid set-up and measurement.

In sum, in certain embodiments of the measurement systems where sample is a human head, the system may determine, based on at least a single determined phase difference and/or multiple differences measured over time, one or more of: rate of skull volume expansion, total fluid volume present in the skull, and intracranial pressure. The below sections further examine information that may be provided by example systems.

Relationships Between Phase Changes and Cranial Vault Dynamics

In the examination of the physiology of skull expansion under intracranial pressure, the CFPPL system analyses may determine time-dependent parameters of significance in intracranial dynamics. Skull expansion results in skull volume changes that have significant implications for fluid volume current (time rate of change in volume) and pressure. Thus, the systems may provide for analysis of the relationships between these quantities and the phase changes measured across the skull.

Cranial Vault Volume

For some example analytic methods, it is assumed that the cranial vault volume, V, is a fraction of the volume of an eccentric ellipsoid as (Equation 5):

$$V = K \frac{4}{3}\pi abc$$

$$V = K \frac{4}{3}\pi \varepsilon_1 \varepsilon_3 b^3$$

where a, b and c are the radii of the ellipsoid, $\varepsilon_1$ and $\varepsilon_3$ are the coefficients of eccentricities along the axes perpendicular to the coronal plane and the horizontal plane respectively, and K is the ratio of cranial vault volume to the ellipsoidal volume. b is the radius measured from the midpoint along the axis perpendicular to the sagittal plane, and is assumed to be in the direction of the ultrasonic propagation. For this example analytic applications, it is assumed that $\varepsilon_1$ and $\varepsilon_3$ do not vary as a and c change (i.e, $d\varepsilon_1/da$ is approximately equal to $d\varepsilon_3/dc$, which is approximately equal to zero). Thus, the calculation of the logarithmic increment in the cranial vault volume $\Delta V/V$ is in terms of the logarithmic increment of phase change as (Equation 6):

$$\frac{\Delta V}{V} = 3\frac{\Delta b}{b} = 3\frac{\Delta \phi}{\phi}$$

where b=1/2.

Cranial Volume Current into Vault Volume

From Equation (6) the change in cranial vault volume as a function of time is (Equation 7):

$$\Delta V(t) = \frac{3V}{\phi_0}\Delta\phi(t)$$

The fluid volume current into the cranial vault, i, is obtained from Equation (7) as (Equation 8):

$$i = \frac{dV}{dt} = \frac{3V}{\phi_0}\frac{d\Delta\phi}{dt}$$

where $dV=d(\Delta V)$. These measurement system examples may therefore measure the skull expansion as a function of time, and the determined net increase of fluid within the cranial vault (net increase of blood and cerebrospinal fluid) is associated with this expansion.

Cranial Pressure Function

Figures 5A, 5B:
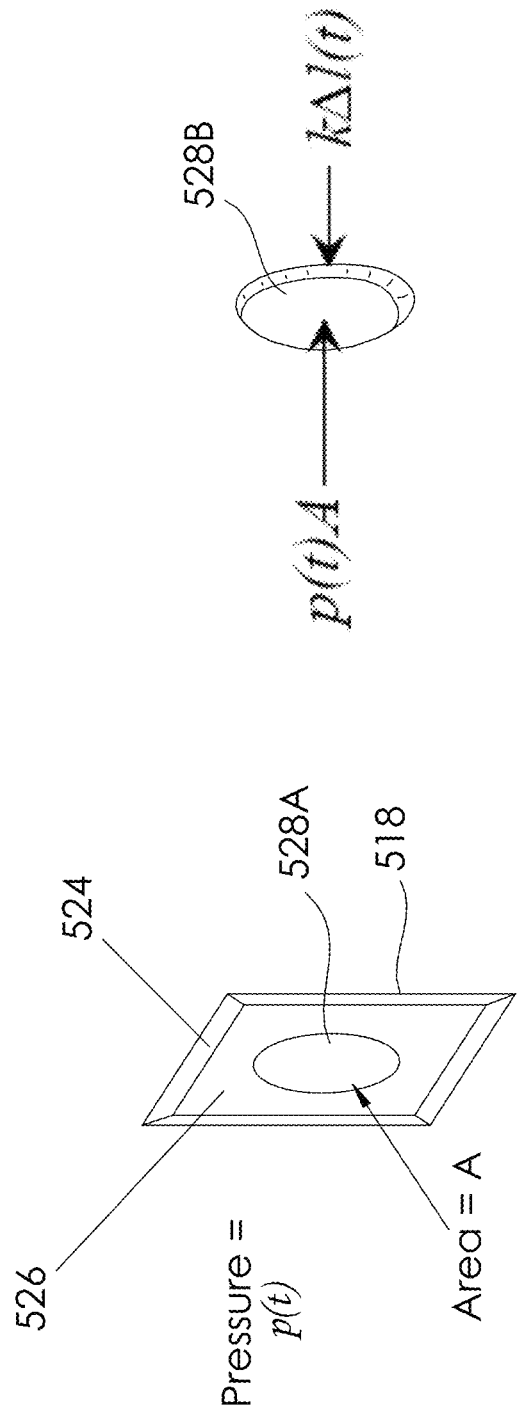
FIGS. 5A and 5B illustrate example sample for analysis by a measurement system and a corresponding force diagram.

The state of skull expansion may be monitored by the phase of the reflected wave received by the transducer in pulse-echo mode. The skull expansion may depend on the pressure inside the skull and the restoring force applied by the skull's elastic properties. FIGS. 5A and 5B illustrate this. FIG. 5A shows the region where the reflection occurs, where the interior, reflecting surface of sample 518 (e.g. a human head containing a skull) is visible. Reflection area 528A is part of the bona dura material 526, which is interior to a skin and/or hair surface 524 area. FIG. 5B is a force diagram corresponding to that reflection segment of skull (528B in this diagram) where the ultrasonic sound beam reflection occurs. FIG. 5 illustrates physical relationships between a segment of skull complex and the pressure p(t) and the displacement, $\Delta l(t)$. In these illustrations, the area A represents the cross-sectional area of the sound beam impinging on the opposite side of the skull from that of ultrasonic pulse insertion. For the freebody diagram showing forces, k is the effective spring constant.

If the radiation pressure increment from the ultrasonic sound beam is neglected, one can write the force on the mass segment shown in FIG. 3(b) as (Equation 9):

$$F(t) = p(t)A - k\Delta l(t)$$

where p(t) is the pressure. From Newton's second law one can write (Equation 10):

$$m\frac{d^2\Delta l(t)}{dt^2} = \sigma A\frac{d^2\Delta l(t)}{dt^2} = p(t)A - k\Delta l(t)$$

where $\sigma$ is the areal mass density of the skull at the reflecting location of the skull and k is the effective spring constant at the site of reflection. Solving the above Equation (10) for pressure, one can obtain (Equation 11):

$$p(t) = \sigma\left[\frac{\partial^2 \Delta l(t)}{\partial t^2}\right] + \frac{k}{A}[\Delta l(t)]$$

The pressure function p(t) is the sum of two parts, each part multiplied by constants. The sum of terms on the right-hand side of Equation (11) may then become the pressure waveform. It should be appreciated that the pressure waveform given by Equation (11) is an absolute physical requirement for the skull expansion variations measured in system examples.

Other Applications

As mentioned above, in some examples, the systems may analyze samples other than a human head/skull, and may further be used to determine other properties than intracranial properties. For example, FIG. 2 shows a schematic diagram of an example embodiment of a system. In this embodiment, the system utilizes operating parameters and components for measuring/evaluating bond characteristics of a sample, e.g. bond characteristics between two dissimilar, bonded materials. The materials may have different thermodynamic states as the test conditions.

In this example, the system 200 includes a processor (one or more additional processors may be incorporated as well) 202 and a digital oscillator module 204. The oscillator module may include a plurality of direct digital synthesizers. For example, oscillator module 204 includes a first direct digital synthesizer 206 and a second direct digital synthesizer 208. The example system also includes a linear phase detector 110, a tone-burst module 212, a transducer 214 communicatively coupled to the tone-burst module and configured to be attached to a sample, and memory 216 communicatively coupled to at least the processor 202. In this example, the transducer 214 may be configured to be attached to an article 218, the article having a bond 222. The bond may be, for example, a liquid phase, gel or adhesive material. The bond may provide a pathway for stress and, therefore, acoustic wave transmission across boundaries. Bonds that are used to transmit stress in structures may have weak areas that lead to premature failure. In some examples, the effects of these regions may be detected using the systems and methods described herein. In this example and other embodiments, the sample may be present in an analysis chamber 220, such as a thermodynamic environmental control chamber. Similar to the above systems, system 200 may determine, based on a plurality of determined phase differences, one or more bond characteristics of the article 218. These system examples may be used to research and examine small phase changes caused by variation of bonding responses to pressure, temperature, and other environmental variables. In some examples, the systems may evaluate and record the stress on a bond vs. time, the strain vs. time, bond temperature vs. time, or a combination thereof. If desired, it is contemplated that the time parameter may be eliminated such and system may determine time-independent information, such as bond modulus vs. temperature. In this example, the DDS components are set to a reference frequency of 10 Mhz, which DDS 1 has zero shift and DDS 2 has a relative phase shift.

Figure 3:
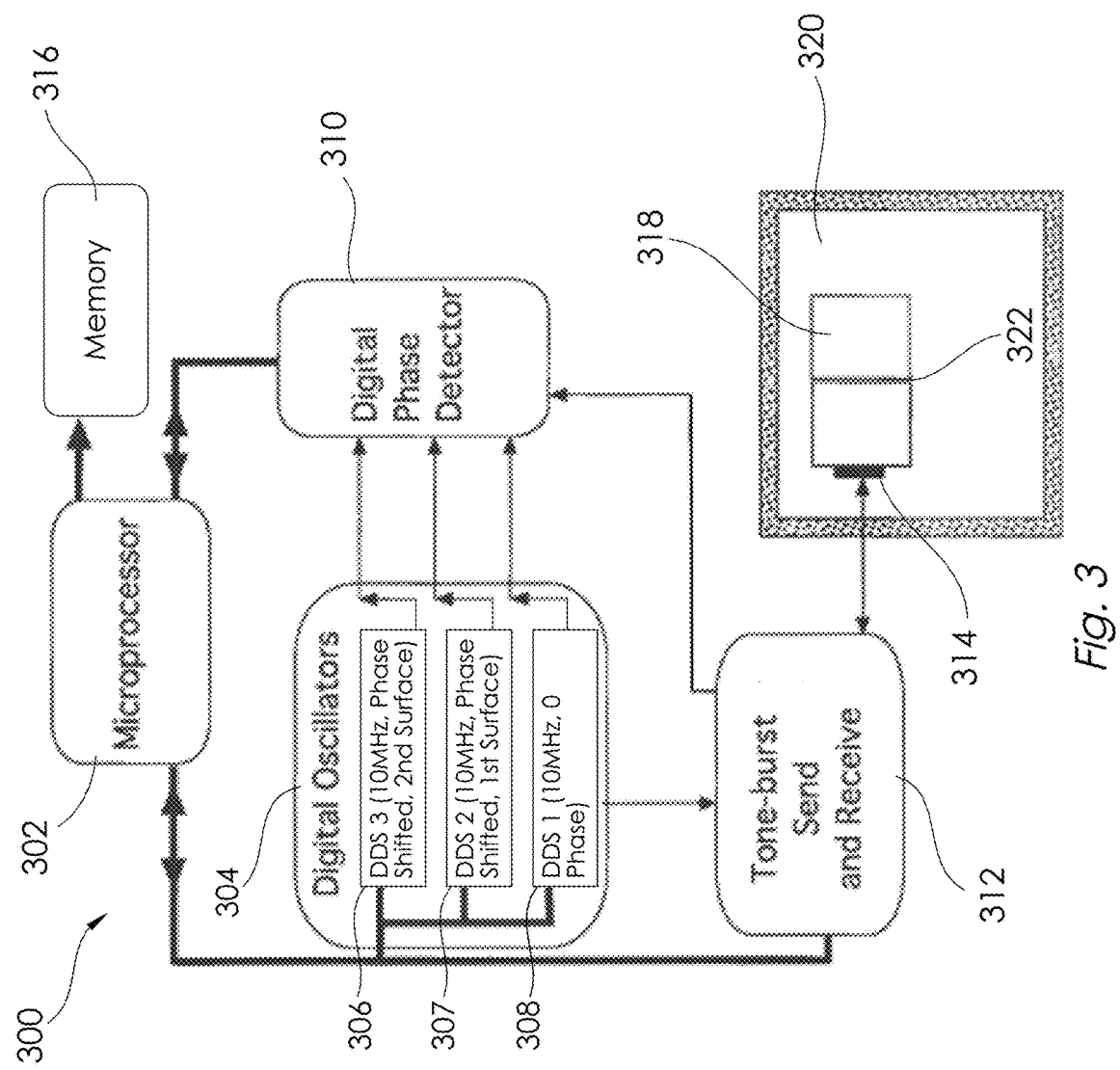
FIG. 3 illustrates a schematic diagram of another example embodiment of a measurement system.

FIG. 3 shows a schematic diagram of another example embodiment of a system, similar to the embodiment of FIG. 2 but further including a third direct digital synthesizer 306. In this example, the second and third DDS components (306 and 307) are both phase shifted, and are associated with a second surface and first surface, respectively. A first received marker on the marked tone-burst may enable first to second DDS phase determination related to the first surface (sent to the DDS 2 phase shift), and turn on the counter, while the second received marks enables first to third DDS phase determination related to the second surface (sent to the DDS-3 phase shift) and turns off the counter. In this manner, both surfaces on the side of the bond 322 may be examined. In some examples, the system may scan along the received wave and measure the change in phase due to multiple reflections from bonding surfaces, where the possibility of resolving these surfaces in time depends on the Nyquist frequency.

In accordance with another example aspect of the disclosure, measurement methods are disclosed. In some examples, the methods include generating, with a first direct digital synthesizer, a reference waveform having a constant frequency, and generating, using a second direct digital synthesizer, a measurement waveform having the same constant frequency as the reference waveform and an initial phase shift relative to the reference waveform. In some examples, the methods then include determining, based on the reference waveform, a tone-burst wave sequence, and subsequently sending, using a transducer, and based on the determined tone-burst wave sequence, a tone-burst into a sample and consequently receiving, using the transducer, a received tone-burst from the sample.

Next, example embodiments include determining a phase difference between the received tone-burst and the measurement waveform and adjusting, using the second digital synthesizer, the initial phase shift of the measurement waveform, by the determined phase difference, to an adjusted phase shift relative to the reference waveform, such that there is no longer any phase difference between the received tone-burst and the measurement waveform.

In certain examples, the methods also include sending, using the transducer, a plurality of additional tone-bursts into the sample, and consequently receiving, using the transducer, a plurality of received tone-bursts. Then, the methods may include determining a plurality of phase differences between the plurality of received tone-bursts and the measurement waveform, wherein the phase shift of the measurement waveform is further adjusted, using the second digital synthesizer, after each tone-burst is received and prior to the subsequent tone-burst being sent into the sample. The adjustment may be based on the determined phase difference between the measurement waveform and the most recently received tone-burst, such that there is no longer any phase difference between the most recently received tone-burst and the adjusted measurement waveform.

In some embodiments, the sample is a human head, and the methods include determining, based on at least the plurality of determined phase differences, one or more of rate of skull volume expansion, total fluid volume present in the skull, and intracranial pressure. In some examples, a delay between the plurality of additional tone-bursts is 20 milliseconds or less, while in other it is 8 milliseconds or less. The delay may depend on the time required for reflected signal to be received.

In certain method examples, the methods include generating, with a first direct digital synthesizer, a reference waveform having a constant frequency, and generating, using a second direct digital synthesizer, a measurement waveform having the same constant frequency as the reference waveform and an initial phase shift relative to the reference waveform. In these examples, the methods may then include sending, using a transducer, a plurality of tone-bursts into a sample and receiving, using the transducer, a plurality of received tone-bursts from the sample. Next, in these embodiments, the methods may include determining a plurality of phase differences between the received tone-bursts and the measurement waveform. In these examples, the phase shift of the measurement waveform is continually updated, using the second digital synthesizer, after each tone-burst is received and prior to the subsequent tone-burst being sent into the sample, such that there is no longer any phase difference between the most recently received tone-burst and the updated measurement waveform.

These system and method descriptions are merely examples. In certain embodiments, the system includes additional combinations and/or substitutions of some or all of the components described above. Likewise, in certain embodiments, the system includes additional steps and/or substitutions (or even elimination) of some or all of the steps described above. Moreover, additional and alternative suitable variations, forms and components for the system will be recognized by those skilled in the art given the benefit of this disclosure. Finally, what's more any of the features discussed in the example embodiments of the method may be features of embodiments of the system (or components thereof), and vice versa.

What is claimed is:

1. An measurement system comprising:
a processor;
a linear phase detector;
a tone-burst module;
a transducer communicatively coupled to the tone-burst module and configured to be attached to a sample;
a digital oscillator module comprising at a first direct digital synthesizer and a second direct digital synthesizer, wherein:
the first direct digital synthesizer is configured to output a reference waveform having a constant frequency when the transducer is attached to a sample; and
the second direct digital synthesizer is configured to output a measurement waveform having the same constant frequency as the reference waveform and an initial phase shift relative to the reference waveform; and
wherein the processor, the digital oscillator module, the linear phase detector, and the tone-burst module are all communicatively coupled to each other; and
a non-transitory computer-readable medium comprising computer-readable instructions that, when executed by the processor, cause the processor to at least:
generate via the first direct digital synthesizer, a reference waveform having a constant frequency when the transducer is attached to a sample;
generate via second direct digital synthesizer, a measurement waveform having the same constant frequency as the reference waveform and an initial phase shift relative to the reference waveform;
determine, using the tone-burst module, and based on the reference waveform, a tone-burst wave sequence;
transmit via the transducer, a tone-burst into the sample that is based, at least in part, on the determined tone-burst wave sequence;
receive, using the transducer, a received tone-burst from the sample;
determine, using the linear phase detector, a phase difference between the received tone-burst and the measurement waveform; and
in response, adjust, using the second digital synthesizer, the initial phase shift of the measurement waveform, by the determined phase difference, to an adjusted phase shift relative to the reference waveform, such that there is no longer any phase difference between the received tone-burst and the measurement waveform.

2. The system of claim 1, wherein non-transitory computer-readable medium further comprises instructions, that when executed by the processor, further cause the processor to at least:
convert, using the linear phase detector, the determined phase difference, a total phase difference between the adjusted measurement waveform and the reference waveform, or both, to a first digital value; and
record, using the processor, the first digital value in the computer-readable medium.

3. The system of claim 1, wherein the non-transitory computer-readable medium further comprises instructions, that when executed by the processor, further cause the processor to at least:
send, using the transducer, and based on the tone-burst wave sequence, a plurality of additional tone-bursts into the sample;
receive, using the transducer, a plurality of received tone-bursts;
determine, using the linear phase detector, a plurality of phase differences between the plurality of received tone-bursts and the measurement waveform; and
wherein the phase shift of the measurement waveform is further adjusted, using the second digital synthesizer, after each tone-burst is received and prior to the subsequent tone-burst being sent into the sample, wherein the adjustment is based on the determined phase difference between the measurement waveform and the most recently received tone-burst, such that there is no longer any phase difference between the most recently received tone-burst and the adjusted measurement waveformnn.

4. The system of claim 3, wherein the non-transitory computer-readable medium further comprises instructions, that when executed by processor, further cause the processor to at least:
convert, using the linear phase detector, the plurality of determined phase differences, a plurality of total phase differences between the adjusted measurement waveforms and the reference waveform, or both, to a plurality of digital values; and
record, using the processor, the plurality of digital values in the computer-readable medium.

5. The system of claim 1, wherein the constant frequency is between 100 KHz and 15 MHz.

6. The system of claim 1, wherein the sample is a human head, and wherein the non-transitory computer-readable medium further comprises instructions, when executed by the processor, further cause the processor to determine, based on at least the determined phase difference, one or more of: rate of skull volume expansion, total fluid volume present in the skull, and intracranial pressure.

7. The system of claim 1, wherein the sample is an article comprising two dissimilar, bonded materials, and wherein the non-transitory computer-readable medium further comprises instructions, that when executed by the processor, further cause the system to determine, based on at least the determined phase difference, one or more bond characteristics.

8. The system of claim 4, wherein the non-transitory computer-readable medium further comprises instructions, that when executed by the processor, further cause the system to record a digital value every ten milliseconds or less.

* * * * *